United States Patent [19]

Gutsche et al.

[11] 4,057,545

[45] Nov. 8, 1977

[54] IMIDAZOLE DERIVATIVES

[75] Inventors: Klaus Gutsche, Rellingen;
Friedrich-Wilhelm Kohlmann; Peter Scharwächter, both of Moorrege, all of Germany

[73] Assignee: Nordmark-Werke GmbH Hamburg, Uetersen, Germany

[21] Appl. No.: 733,349

[22] Filed: Oct. 18, 1976

[30] Foreign Application Priority Data

Nov. 6, 1975 Germany ................... 2549798

[51] Int. Cl.$^2$ ............... C07D 233/56; C07D 233/64
[52] U.S. Cl. ..................... 542/428; 424/273 R; 548/335
[58] Field of Search ........ 260/240 F, 240 R, 240 CA, 260/309; 424/273

[56] References Cited

U.S. PATENT DOCUMENTS

| | | | |
|---|---|---|---|
| 3,812,109 | 5/1974 | Shen et al. | 260/240 R |
| 3,927,017 | 12/1975 | Heeres et al. | 424/273 |
| 3,992,403 | 11/1976 | Roebke | 424/273 |
| 4,006,243 | 1/1977 | Strehlke et al. | 424/273 |
| 4,013,643 | 3/1977 | Nysted | 260/240 R |

*Primary Examiner*—Arthur P. Demers
*Attorney, Agent, or Firm*—McNenny, Pearne, Gordon, Gail, Dickinson & Schiller

[57] ABSTRACT

The present invention is related to new imidazole derivatives having the general formula

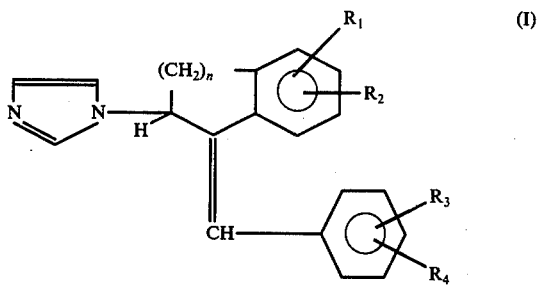

The invention is further related to a process for controlling fungi, yeasts and bacteria in humans and animals by administering orally or externally a compound of the above general formula to a human or animal suffering from such fungi, yeasts or bacteria.

9 Claims, No Drawings

IMIDAZOLE DERIVATIVES

This invention relates to new imidazole derivatives corresponding to the general formula

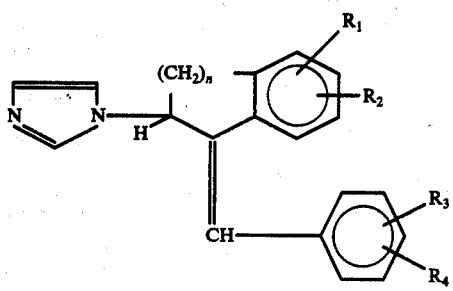

(I)

in which $R_1$, $R_2$, $R_3$ and $R_4$, which may be the same or different, represent hydrogen, chlorine, bromine, lower alkyl groups with 1 to 4 carbon atoms or lower alkoxy groups with 1 to 4 carbon atoms (especially $C_1$–$C_4$ n-alkyl and n-alkoxy groups), and n is an integer from 0 to 2, the valencies liberated being saturated by hydrogen where $n = 0$, and to their pharmacologically compatible salts with the usual acids.

Preferred compounds of formula I are those in which $R_1$, $R_2$, $R_3$ and $R_4$, which may be the same or different, represent hydrogen, chlorine, bromine, methyl or methoxy and n is an integer from 0 to 2, the valencies liberated being sataurated by hydrogen where $n = 0$, and also their pharmacologically compatible salts with the usual acids.

Particularly preferred compounds of formula I are those in which the substitutents $R_1$ and $R_2$ or $R_3$ and $R_4$ are in the 2- and/or 4-position to the bond to the propene double bond, so that the compounds correspond to the general formula

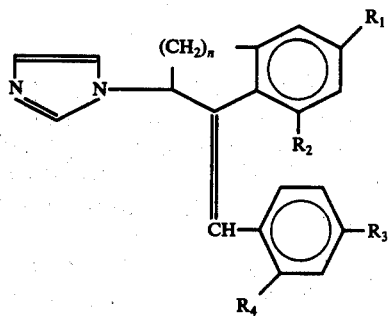

(II)

Other preferred compounds of general formula I are those in which $n = 0$, in which case the valencies liberated are saturated by hydrogen, and also their pharmacologically compatible salts with the usual acids. These compounds correspond to the general formula

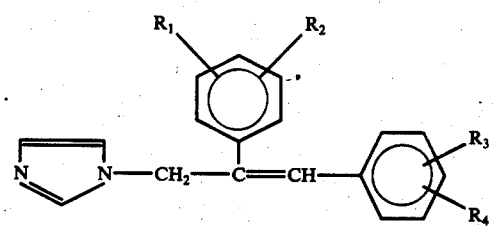

(III)

Other particularly preferred compounds of formula III are those in which $R_1$, $R_2$, $R_3$ and $R_4$, which may be the same or different, represent hydrogen, chlorine, bromine, methyl or methoxy, and especially those compounds of formula III in which the substitutents $R_1$ and $R_2$ or $R_3$ and $R_4$ are in the 2- and/or 4-position, so that they correspond to the general formula

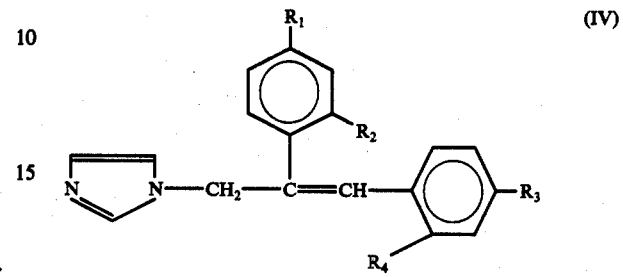

(IV)

The new compounds may be present in the form of transor cis-isomers or mixtures thereof.

The usual acids used for forming pharmacologically compatible salts are, for example, hydrochloric acid, nitric acid, sulphuric acid, phosphoric acid, acetic acid, lastic acid, citric acid and salicylic acid. However, it is peferred to use the above-mentioned inorganic acids, especially nitric acid or hydrochloric acid, which form with the compounds according to the invention salts that crystallize particularly well.

The new compounds and their salts are valuable agents for controlling fungi and yeasts and, in addition, are also active against several types of bacteria. To test the antimicrobial activity of the new compounds in vitro, they were tested in a series dilution test with dilutions of from 1:10,000 to 1:100,000 for their effectiveness against the germs Staphylococcus aureus, Trichophyton mentagrophytes and Candida albicans. The result of a selection is shown in Table 1.

Table 1

| n | $R_1$ | $R_2$ | $R_3$ | $R_4$ | Staph. aur. | Trichoph. | Cand. alb. |
|---|-------|-------|-------|-------|-------------|-----------|------------|
| 0 | 4-CH₃ | H | 2-Cl | 4-Cl | φ φ | φ φ | φ (+) |
| 0 | 4-Cl | H | 4-Br | H | φ φ | φ φ | ++ |
| 0 | 4-Cl | 2-Cl | 4-Cl | 3-Cl | φ φ | φ φ | φ |
| 0 | 4-Cl | H | 4-Cl | H | φ φ | φ φ | ++ |
| 0 | 4-Cl | 2-Cl | 4-Br | H | φ φ | φ φ | (+) |
| 0 | 4-Br | H | 4-Br | H | φ φ | φ φ | ++ |
| 0 | 4-Br | H | 4-Br | H | φ φ | φ φ | φ |
| 1 | 6-Cl | H | 4-Cl | H | φ φ | φ φ | ++ |
| 1 | 6-Cl | H | 4-Cl | 2-Cl | φ φ | φ φ | ++ |
| 1 | H | H | H | 4-Cl | φ φ | φ φ | +++ |
| 1 | H | H | 3-Cl | 4-Cl | φ φ | φ φ | φ |
| 2 | H | H | H | 4-Cl | φ φ | φ φ | ++ |
| 2 | H | H | H | H | φ φ | φ φ | ++ |
|   |      |      |      |     | φ | φ | φ +++ |

Table 1-continued

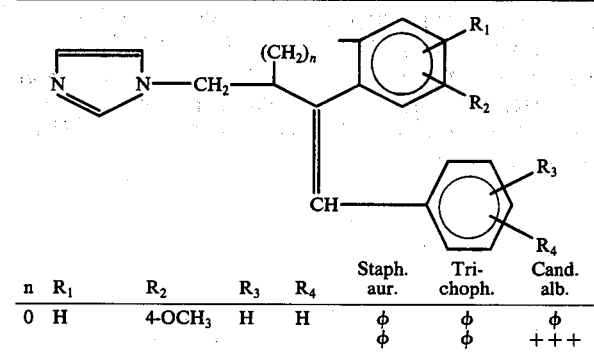

| n | R₁ | R₂ | R₃ | R₄ | Staph. aur. | Tri- choph. | Cand. alb. |
|---|----|----|----|----|----|----|----|
| 0 | H | 4-OCH₃ | H | H | φ φ | φ φ | φ +++ |

1st value at 1: 10,000
2nd value at 1: 100,000
φ complete inhibition
(+) strong inhibition
+ moderate inhibition
++ slight inhibition
+++ no inhibition For comparable activities against fungi, yeasts and bacteria as determined by the tube dilution test, the new compounds are distinctly superior to the imidazole derivative Miconazole (1-[2,4-dichloro-β-(2,4,-dichlorobenzyloxy)-phenethyl]-imidazole nitrate), recently introduced into medicinal practice, in an animal test conducted an Candida-infected mice. Accordingly, the compounds according to the invention are particularly suitable for the oral treatment of generalized infections by fungi and yeasts in human and veterinary medicine. Since the hitherto available medicaments are not yet satisfactory (Lit.: Infection 2, (1974) 95–107), they represent a valuable addition to pharmacology. In addition, they may be used equally effectively for the local treatment of surface infections and for the treatment of infections of the mucosa excessible to local treatment. Typical diseases of thiskind, for the treatment of which the compounds of the present invention are particular useful, are for instance generalized candidoses, candidoses of the lungs, of the skin or of the genitals or generalized trichophytoses (tineas) or trichophytoses of the skin, of the nails or of the hair.

In order to determine the oral effectiveness of the compounds, groups of 10 mice each weighing approximately 20 g were each treated i.m for 2 days with 50 mg/kg of hydrocortisone to ensure effective development of the infection. The mice were then each infected i.v. with 500,000 Candida albicans germs and thereafter were treated twice daily for 7 days with 100 mg/kg of the substance to be tested. In addition to an infected, but untreated control group, one group was treated with the reference substance Miconazole for comparison. As can be seen from Table 1, up to 100 % of the animals treated with the new compounds were still alive on the last day of the treatment, whereas only 20 % of the animals in the control group and those treated with Miconazole were still alive on the last day.

Table 2

| Sub- stance | Number of surviving animals | | | | | | | LD₅₀ (mice) |
|---|---|---|---|---|---|---|---|---|
| | 1 | 2 | 3 | 4 | 5 | 6 | 7 ← | |
| A | 10 | 10 | 10 | 10 | 10 | 9 | 9 | approx. 1000 mg/kg |
| B | 10 | 10 | 10 | 10 | 10 | 10 | 10 | approx. 1000 mg/kg |
| C | 10 | 10 | 10 | 9 | 9 | 8 | 5 | approx. 1000 mg/kg |
| D | 10 | 10 | 10 | 9 | 9 | 8 | 7 | approx. 1000 mg/kg |

Table 2-continued

| Sub- stance | Number of surviving animals | | | | | | | Days after infection | LD₅₀ (mice) |
|---|---|---|---|---|---|---|---|---|---|
| | 1 | 2 | 3 | 4 | 5 | 6 | 7 ← | | |
| E | 10 | 10 | 10 | 9 | 7 | 6 | 6 | | approx. 2000 mg/kg |
| F | 10 | 10 | 10 | 10 | 10 | 9 | 9 | | approx. 2000 mg/kg |
| G | 10 | 10 | 10 | 10 | 9 | 8 | 7 | | approx. 1000 mg/kg |
| Control | 10 | 9 | 5 | 2 | 2 | 2 | 2 | | |
| Miconazole | 10 | 10 | 8 | 8 | 6 | 4 | 2 | | 578 mg/kg (Lit.) |

A = 1-(2,4-dichlorophenyl)-2-(4-chlorophenyl)-3-(imidazolyl-1)-propene-1-nitrate
B = 1-(4-chlorophenyl)-2-(4-chlorophenyl)-3-(imidazolyl-1)-propene-1-nitrate
C = 1-phenyl-2-(4-chlorophenyl)-3-(imidazolyl-1)-propene-1-nitrate
D = 1-(2,4-dichlorophenyl)-2-phenyl-3-(imidazolyl-1)-propene-1-nitrate
E = 1,2-bis-(2,4-dichlorophenyl)-3-(imidazolyl-1)-propene-1-nitrate
F = 1-(4-chlorophenyl)-2-(2,4-dichlorophenyl)-3-(imidazolyl-1)-propene-1-nitrate
G = 1-(4-bromophenyl)-2-(2,4-dichlorophenyl)-3-(imidazolyl-1)-propene-1-nitrate.

The LD₅₀-values approximately 2 to 4 times higher than those obtained with the reference substance show another advantage of the new compounds.

The new compounds are administered orally in the form of, for example, dragees, liquids, capsules or tablets in doses of from 0.5 to 100 mg/kg of body weight, and externally in the form of ointments, creams, emulsions, solutions and powders which contain from 0.1 to 10 % of the active compound. In addition, these formulations also contain standard pharmaceutical additives.

The new compounds of formula I are prepared in known manner by reacting a ketone corresponding to the general formula

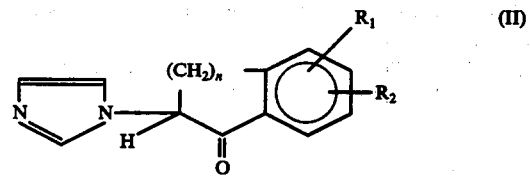

in which R₁, R₂ and n have the same meaning as in formula I, by the methods of Wittig's carbonyl olefinization, such as are described in numerous variants known to the expert, for example in Organ. Reactions, Vol. 14, Chapter 3, pages 270–490 or in Houben-Weyl, Methoden der organischen Chemie, Vol. 5/1b, pages 383–418, with a phosphorus derivative corresponding to the general formula IIa

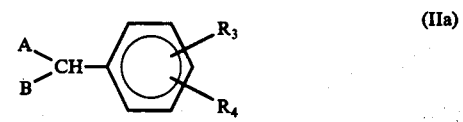

in which R₃ and R₄ have the same meaning as in formula I and A and B either together represent the groupment of the general formula IIb

or A is the groupment of the general formula IIc

and B is an ionically bound alkali metal, in said formulas IIb and IIc.

$R_5$, $R_6$ and $R_7$, which may be the same or different, but are preferably the same, represent the phenyl radical, the p-carboxyphenyl radical, the p-dimethylaminophenyl radical, the dimethylamino, piperidino or morpholino group, lower alkyl radicals with 1 to 3 carbon atoms or the cyclohexyl radical, and $R_8$ and $R_9$ which may be the same or different, but are preferably the same, represent lower alkoxy groups with 1 to 3 carbon atoms or phenyl radicals.

Thus, the compounds of formulas IIa and IIb are correspond to general formula III

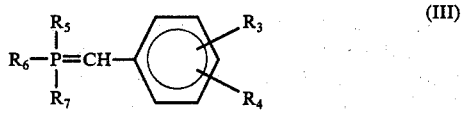

and those of formulas IIa and IIc correspond to the general formula IV

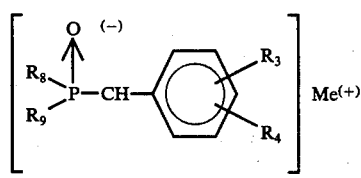

Me being the alkali metal.

$R_5$, $R_6$ and $R_7$ in formula IIb preferably represent phenyl radicals.

Compounds of general formulas IIa and IIc (= formula IV) in which $R_8$ and $R_9$ represent alkoxy groups, are particularly preferred.

The compounds of general formula IIa are generally not isolated, but instead are reacted with the ketones of general formula II in a solvent after their production. In special cases, however, the compounds of general formulae IIa and IIb (= formula III) may even be isolated and reacted with the ketones of general formula II in the absence of a solvent, which can be advantage for obtaining relatively high reaction temperatures.

The solvents which may be used for producing the compounds of general formulae I and IIa are known to the expert from the literature and may be, for example, various ethers, such as diethyl ether, tetrahydrofuran or ethylene glycol dimethyl ether, alcohols, hydrocarbons such as hexane or benzene, dimethyl sulphoxide and dimethyl formamide or even liquid ammonia. Depending upon the conditions applied, the compounds of formula I according to the invention are obtained in the form of a mixture of cis- and trans-isomers which, if desired, may be split up into the isomers by standard methods, for example by fractional crystallization, or alternatively the compounds of formula II are obtained from the outset in the form of cis- or trans-isomers. Standard bases used for the production of the compounds of general formula IIa may be, for example, lithium phenyl, lithium butyl, alkali alcoholates, sodium amide, sodium hydride or sodium dimethyl sulphoxylate.

All the reaction conditions and auxiliaries mentioned by way of example are not intended to represent any limitation by comparison with the methods known from the literature.

For medicinal purposes, the compounds according to the invention are used in the form of the bases of formula I or in the form of the salts in standard pharmaceutical formulations, for example in form of ointments, creams, solutions, emulsions, powders and aerosols for external application, or in the form of tablets, dragees, capsules, solutions, emulsions, suppositories or ovuli for internal application, the usual pharmaceutical excipients being employed for the preparation of these formulations. The composition of the medicaments according to the invention is preferably such that they consist of one or more compounds of formula I or their pharmacologically compatible salts with acids and standard pharmaceutical additives.

The invention is illustrated by the following Examples.

EXAMPLE 1

4 g of 2,4-dichlorobenzyl triphenyl phosphonium chloride and 2.2 g of 2,4-dichloro-omega-(imidazolyl-1)-acetophenone are dissolved in 100 ml of methanol. A solution of 0.2 g of sodium in 10 ml of methanol is then added and the whole boiled under reflux for 2 hours. After the solvent has been distilled off, the residue is dissolved in ethylacetate and freed from undissolved sodium chloride by filtration. 3.1 g (74 % of the theoretical) of a cis-trans-isomer mixture of 1,2-bis(2,4-dichlorophenyl)-3-(imidazolyl-1 l)-propene-1-nitrate melting at 145°–152° C are obtained from the ethylacetate solution by the gradual addition of a slight excess of 100 % nitric acid. Approximately 2 g of the trans-isomer melting at 159°–160° C are obtained therefrom by recrystallization from benzene.

EXAMPLE 2

3 g of lithium butyl (20 % in hexane) are added to 4 g of 2,4-dichlorobenzyl triphenyl phosphonium chloride in 100 ml of absolute tetrahydrofuran. After stirring for 3 hours at room temperature, 2.3 g of 4-bromo-omega-(imidazolyl-1)-acetophenone in 50 ml of tetrahydrofuran are added to the resulting solution of the 2,4-dichlorobenzylidene-triphenyl phosphorane, after which the whole is boiled under reflux for 5 hours. The tetrahydrofuran is then distilled off, the residue is dissolved in ethylacetate, filtered and the product precipitated from the resulting solution with nitric acid in the same way as in Example 1. Recrystallization from n-butanol give 3 g (72 % of the theoretical) of trans-1-(4-bromophenyl)-2-(2,4-dichlorophenyl)-3-(imidazolyl-1)-propene-1-nitrate melting at 201° C.

EXAMPLE 3

2.6 g of 4-chlorobenzyl phosphonic acid diethyl ester, 2.3 g of 2-(imidazolyl-1)-6-chloro-1-indanone and 2 g of potassium tert.-butanolate are dissolved in 100 ml of benzene and the resulting solution boiled under reflux for 10 hours. After cooling, the solution is poured onto ice water, the benzene phase is separated off and thoroughly dried with potassium carbonate. Precipitation with ethereal nitric acid gives 3.3 g (82 % of the theoretical) of 1-(4-chlorobenzylidene)-2-(imidazolyl-1)-6-chloroindane nitrate which, after recrystallization from ethanol/isopropyl ether, is obtained in the form of the pure trans-isomer with a melting point of 137°-140° C.

The following compounds are similarly produced:

cis-1-(4-chlorophenyl)-2-(2,4-dichlorophenyl)-3-(imidazolyl-1)-propene-1-nitrate; m.p.: 175° C.

trans-1-(4-chlorophenyl)-2-(2,4-dichlorophenyl)-3-(imidazolyl-1)-propene-1-nitrate; m.p.: 160° C.

cis-1,2-bis-(2,4-dichlorophenyl)-3-(imidazoly-1)-propene-1-nitrate; m.p.: 155° C trans-1-phenyl-2-(2,4-dichlorophenyl)3-(imidazolyl-1)-propene-1-nitrate; m.p.: 150° C trans-1-(3,4-dichlorophenyl)-2-(2,4-dichlorophenyl)-3-(imidazolyl-1)-propene-1-nitrate; m.p.: 198° C trans-1-(2,4-dichlorophenyl)-2-(4-chlorophenyl)-3-(imidazoly-1)-propene-1-nitrate; m.p.: 178° C cis-1-(2,4-dichlorophenyl)-2-(4-chlorophenyl)-3-(imidazoly-1)-propene-1-nitrate; m.p.: 160° C cis, trans-1-phenyl-2-(4-chlorophenyl)-3-(imidazolyl-1)-propene-1-nitrate; m.p.: 144° C cis, trans-1-(4-chlorophenyl)-2-(4-chlorophenyl)-3-(imidazolyl-1)-propene-1-nitrate; m.p.: approx. 160° C cis, trans-1-(2,4-dichlorophenyl)-2-phenyl-3-(imidazolyl-1)-propene-1-nitrate; m.p.: approx. 150° C trans-1-(4-chlorophenyl)-2-phenyl-3-(imidazolyl-1)-propene-1nitrate; m.p.: 156° C cis-1,2-diphenyl-3-(imidazolyl-1)-propene-1-nitrate; m.p.: 145° C cis, trans-1,2-diphenyl-3-(imidazolyl-1)-propene-1-nitrate; m.p.: 150° C cis, trans-2-(imidazolyl-1)-1-(2,4-dichlorobenzylidene)-indancenitrate; m.p.: 178° C trans-2-(imidazolyl-1)-1-(4-chlorobenzylidene)-indane-nitrate; m.p.: 190° C trans-2-(imidazoly-1)-1-benzylidene-indane-nitrate; m.p.: 150° C trans-1-(2,4-dichlorobenzylidene)-2-(imidazolyl-1)-6-chloroin-danenitrate; m.p.: 163° C cis, trans-1-benzylidene-2-(imidazolyl-1)-tetralin-nitrate; m.p.: 146° C trans-1-benzylidene-2-(imidazolyl-1)-tetralin-nitrate; m.p.: 151° C cis, trans-1-(4-chlorobenzylidene)-2-(imidazolyl-1)-tetralin-nitrate; m.p.: 180° C trans-1-(4-chlorobenzylidene)-2-(imidazoly-1) tetralin-nitrate; m.p.: 185° C trans-1-(2,4-dichlorophenyl)-2-(4-methylphenyl)-3-(imidazolyl-1)-propene-1-nitrate; m.p. 135° C trans-1-(4-chlorophenyl)-2-(4-methylphenyl)-3-(imidazolyl-1)-propene-1-nitrate; m.p.: 176° C cis, trans-1-(4-chlorophenyl)-2-(4-methylphenyl)-3-(imidazolyl-1)-propene-1-nitrate; m.p.: 150° C cis, trans-1-(2,4-dichlorophenyl)-2-(4-methylphenyl)-3-(imidazolyl-1)-propene-1-nitrate; m.p.: 136° C trans-1-phenyl-2-(4-methoxyphenyl)-3-(imidazoly-1)-propene-1- nitrate; m.p.: 170° C trans-1-(4-bromophenyl)-2-(2,4-dichlorophenyl)-3-(imidazolyl-1)-propene-1-nitrate; m.p.: 201° C cis, trans-1-(4-chlorophenyl)-2-(4-bromophenyl)-3-(imidazolyl-1)-propene-1-nitrate; m.p.: 160° C trans-1-(4-chlorophenyl)-2-(4-bromophenyl)-3-(imidazoly-1)-propene-1-nitrate; m.p.: 172° C cis, trans-1-phenyl-2-(4-bromophenyl)-3-(imidazolyl-1)-propene-nitrate; m.p. 145° C trans-1-phenyl-2-(4-bromophenyl)3-(imidazolyl-1)-propene-1-nitrate; m.p.: 180° C cis, trans-1-(4-bromophenyl)-2-(4-chlorophenyl)-3-(imidazolyl-1)-propene-1-nitrate; m.p.: 167° C cis, trans-1-(4-bromophenyl)-2-phenyl-3-(imidazolyl-1)-propene-1-nitrate; m.p.: 148° C cis, trans-1,2-bis-(4-bromophenyl)-3-(imidazolyl-1)-propene-1-nitrate; m.p.: 176° C trans-1-(3,4-dichlorobenzylidene)-2-(imidazolyl-1)-indane-nitrate; m.p.: 168° C.

EXAMPLE 4

Tablet containing 250 mg of active principle

| Active principle | 250 g | I |
|---|---|---|
| Potato starch | 100 g | |
| Lactose | 50 g | |
| 4 % gelatin solution | 45 g | II |
| Talcum | 10 g | III |
| 1000 tablets = approx. 410 g | | |

Production

The finely powdered active principle, potato starch and lactose are mixed (= I).

The mixture I is moistened with approximately 45 g of II, finely granulated and dried. the dry granulate is sifted, mixed with 10 g of III and compressed into tablet form in a rotary tabletting machine.

The tablets are introduced into tightly closing containers of polypropylene.

EXAMPLE 5

| Cream containing 2 % of active principle | |
|---|---|
| Active principle | 2.0 g |
| Glycerol monostearate | 10.0 g |
| Cetyl alcohol | 5.0 g |
| Polyethylene glycol-400-stearate | 10.0 g |
| Polyethylene glycol sorbitan monostearate | 10.0 g |
| Propylene glycol | 6.0 g |
| p-Hydroxy benzoic acid methyl ester | 0.2 g |
| Demineralised water | ad 100.0 g |

Production

The very finely powdered active principle is suspended on the propylene glycol and the resulting suspension stirred into a melt, heated to 65° C, of glycerol monostearate, cetyl alcohol, polyethylene glycol-400-sterarate and polyethylene glycol sorbitan monostearate. A solution heated to 70° C of the p-hydroxy benzoic acid methyl ester in water is emulsified into this mixture. After cooling the cream is homogenized in a colloid mill and poured into tubes.

EXAMPLE 6

| Powder containing 2 % of active principle | |
|---|---|
| Active principle | 2.0 g |
| Zinc oxide | 10.0 g |
| Magnesium oxide | 10.0 g |
| Highly disperse silicon oxide | 2.5 g |
| Magnesium stearate | 1.0 g |
| Talcum | 74.5 g |

Production

The active principle is micronised in an air jet mill and mixed homogeneously with the other constituents.

The mixture is sifted through a number 7 screen and introduced into polyethylene containers with a scattering insert.

What we claim is:

1. An inidazole derivative corresponding to the general formula

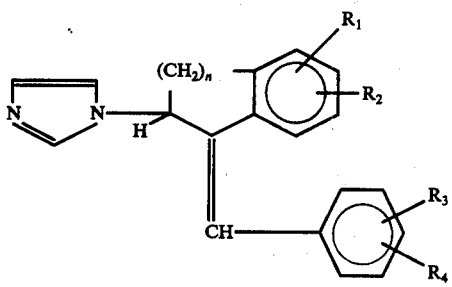

in which $R_1$, $R_2$, $R_3$ and $R_4$, which may be the same or different, represent a member selected from the group consisting of hydrogen, chlorine, bromine, the lower alkyl groups with 1 to 4 carbon atoms and the lower alkoxy groups with 1 to 4 carbon atoms and $n$ is an integer from 0 to 2, the velencies liberated being saturated by hydrogen where $n = 0$, and their pharmacologically compatible salts with acids.

2. 1-(2,4-Dichlorophenyl)-2-(4-chlorphenyl)-3-(imidazolyl-1)-1-propene and its pharmacologically compatible salts with acids.

3. 1-(4-Chlorophenyl)-2-(4-chlorophenyl)-3-(imidazolyl-1)-1-propene and its pharmacologically compatible salts with acids.

4. 1-Phenyl-2-(4-chlorophenyl)-3-(imidazolyl-1)-1-propene and its pharmacologically compatible salts with acids.

5. 1-(2,4-Dichlorophenyl)-2-phenyl-3-(imidazoly-1)-1-propene and its pharmacologically compatible salts with acids.

6. 1,2-Bis-(2,4-dichlorophenyl)-3-(imidazolyl-1)-1-propene and its pharmacologically compatible salts with acids.

7. 1-(4-Chlorophenyl)-2-(2,4-dichlorophenyl)-3-(imidazolyl-1)-1-propene and its pharmacologically compatible salts with acids.

8. 1-(4-Bromophenyl)-2-(2,4-dichlorophenyl)-3-(imidazolyl-1)-1-propene and its pharmacologically compatible salts with acids.

9. 1-(2,4-Dichlorophenyl)-2-(p-tolyl)-3-(imidazolyl-1)-1-propene and its pharmacologically compatible salts with acids.

* * * * *